Figure 1:
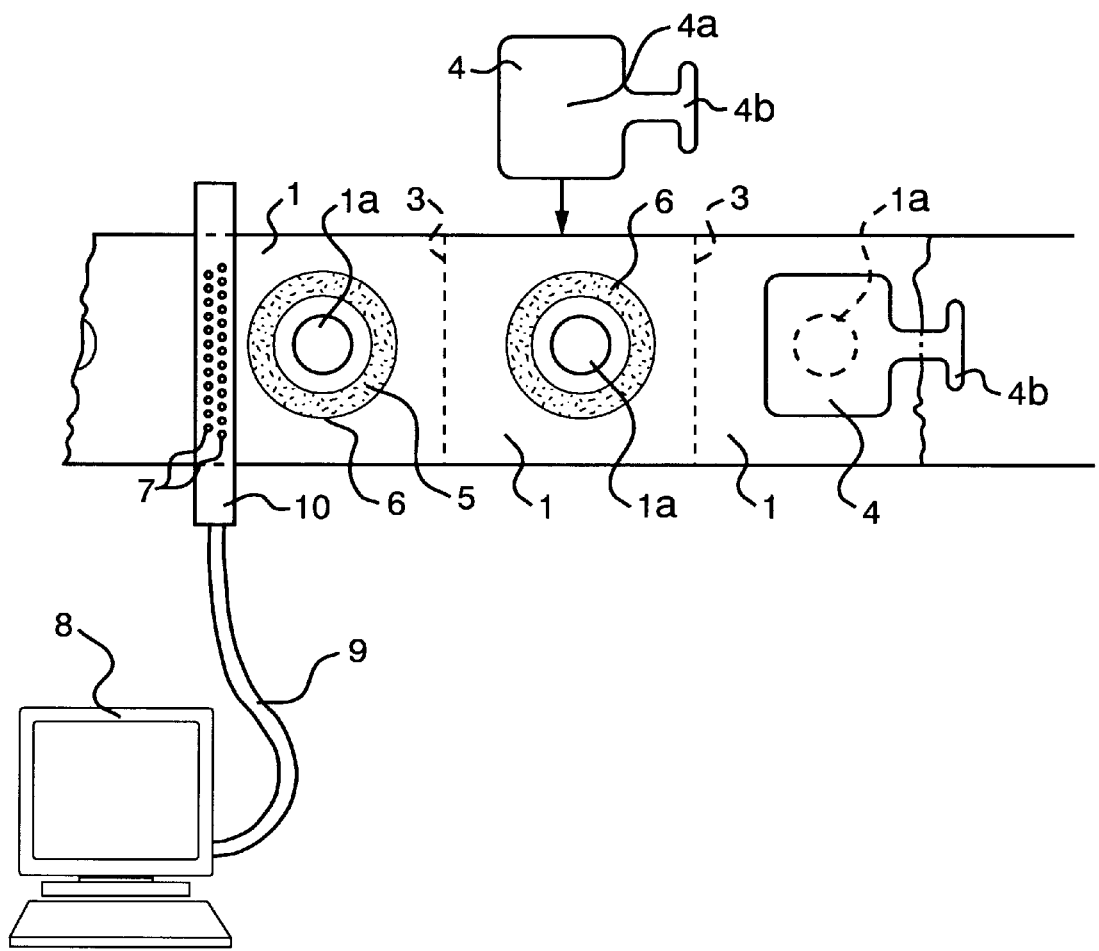

United States Patent [19]
Lang

[11] Patent Number: 6,117,241
[45] Date of Patent: Sep. 12, 2000

[54] APPARATUS FOR MAKING AN ELECTRODE TO BE APPLIED TO THE SKIN

[76] Inventor: Burrhus Lang, Goethestrasse 17/9, A-6020 Innsbruck, Austria

[21] Appl. No.: 08/930,170

[22] PCT Filed: Apr. 9, 1996

[86] PCT No.: PCT/AT96/00068

§ 371 Date: Oct. 9, 1997

§ 102(e) Date: Oct. 9, 1997

[87] PCT Pub. No.: WO96/32057

PCT Pub. Date: Oct. 17, 1996

[30] Foreign Application Priority Data

Apr. 13, 1995 [AT] Austria ............................ 643/95

[51] Int. Cl.[7] ............................................. B05C 7/02
[52] U.S. Cl. .................. 118/696; 118/46; 118/315; 118/325; 156/578
[58] Field of Search ................ 118/696, 46, 301, 118/315, 325; 156/578, 291, 252; 29/886, 885; 600/372, 382; 427/2.12, 2.31, 207.1, 421

[56] References Cited

U.S. PATENT DOCUMENTS

| | | |
|---|---|---|
| 4,687,137 | 8/1987 | Boger . |
| 4,798,642 | 1/1989 | Craighead et al. ..................... 156/252 |
| 5,264,249 | 11/1993 | Perrault . |

FOREIGN PATENT DOCUMENTS

| | | |
|---|---|---|
| 0635239 | 1/1995 | European Pat. Off. . |
| 298616 | 3/1992 | Germany . |
| WO9300857 | 1/1993 | WIPO . |

*Primary Examiner*—Laura Edwards
*Attorney, Agent, or Firm*—Lorusso & Loud

[57] ABSTRACT

A process and device for making an electrode to be applied to the skin in which a carrier provided with an opening is stuck, on the side remote from the skin, to a tag portion which covers the opening. Adhesive is applied to the tag and/or the carrier only on a locally restricted partial region of their facing surfaces and the tag is adhesively secured to the carrier.

3 Claims, 3 Drawing Sheets

APPARATUS FOR MAKING AN ELECTRODE TO BE APPLIED TO THE SKIN

The invention concerns a process and an apparatus for the production of an electrode for application to the skin, in which a carrier provided with an opening is stuck, on the side remote from the skin, to a tag portion which covers over the opening.

Electrodes for application to the skin (for example ECG-electrodes etc), which have a carrier having a central opening which is covered over on the top side thereof by a cover portion (a so-called tag portion) have already long been known. Usually on the underside the carrier has a skin-compatible adhesive which is self-adhesive and which is covered over by a pull-off film or sheet for the purposes of transportation or storage. After the pull-off film or sheet has been pulled off the carrier can be stuck on to the skin of the patient. The tag portion carries an electrical connection to permit the connection of an electrode cable, wherein that outwardly disposed connection (contact region) is electrically connected to the region of the opening of the carrier, which represents the actual sensor region. For example a liquid electrolyte gel in a sponge or a solid conductive gel is applied in that sensor region in order to transmit the electrical currents between the skin and the actual sensor region. From there the currents then pass through the tag portion or along the tag portion outwardly to the contact region.

It is already known for the tag portion to be stuck fast on the carrier by means of an adhesive which is activatable (which is therefore initially non-adhesive). For example it is possible to use a heat-activatable adhesive. Particularly in the case of electrodes in which the contact region is arranged in laterally displaced relationship with the central sensor region on a free projection of the tag portion, there is the basic problem that on the one hand the tag portion is intended to adhere firmly and sealingly everywhere to the carrier, and that on the other hand a good electrical connection is to be made between the sensor region and the laterally displaced contact region through the tag portion or along same. In that respect it is always to be borne in mind that electrodes of this kind are disposable articles and should therefore be of a simple structure and thus inexpensive in terms of production.

In order to satisfactorily solve those problems, the process according to the invention provides that adhesive is applied to the tag portion and/or the carrier only on a locally delimited portion of their mutually facing surface and then the tag portion and the carrier are stuck together.

There is thus in particular the possibility of applying the adhesive only in the region of overlap between the tag portion and the carrier, missing out that region of the tag portion which later comes to lie at the opening of the carrier. Thus it is possible for example to use an electrically conductive tag portion which in the region of the opening of the carrier forms a sensor region which is electrically connected to a laterally displaced contact region preferably provided on a projection of the tag portion. In contrast to a known procedure which involves applying adhesive over the full surface area involved, the locally delimited application of adhesive can prevent the tag portion also being covered over by adhesive in the region of the opening of the carrier. Rather, the sensor region remains free from adhesive and can thus easily contact the skin of the patient, for example by way of a conductive gel.

In principle it would also be possible for the tag portion to be made from electrically insulating material and for an electrically conductive conductor track in layer form to be applied thereto. In that embodiment the electrically insulating tag portion could already be coated with an activatable adhesive prior to the application of the conductor track, or it could consist in general of an adhesively activatable material (for example a thermoplastic material). Such a tag portion can then be glued on to the carrier by activation of the adhesive (for example by heating a melt adhesive or by chemical activation of a chemically activatable adhesive or by UV-irradiation of an UV-activatable adhesive, in which case the conductor track which extends between the layer of adhesive and the carrier ensures good electrical contact between the sensor region in the region of the opening of the carrier and a laterally displaced contact region for the connection of an electrode cable. With the process according to the invention it is now additionally possible for an adhesive to be applied in locally delimited manner in the region of the conductor track in order to ensure that a sealing closure effect is also afforded in the region of the conductor track as between the tag portion and the carrier, whereby in particular a gel disposed in the region of the opening of the carrier cannot escape laterally between the tag portion and the electrode under the conductor track.

Further advantages and details of the invention will be described more fully with reference to the following specific description.

Figure 2:
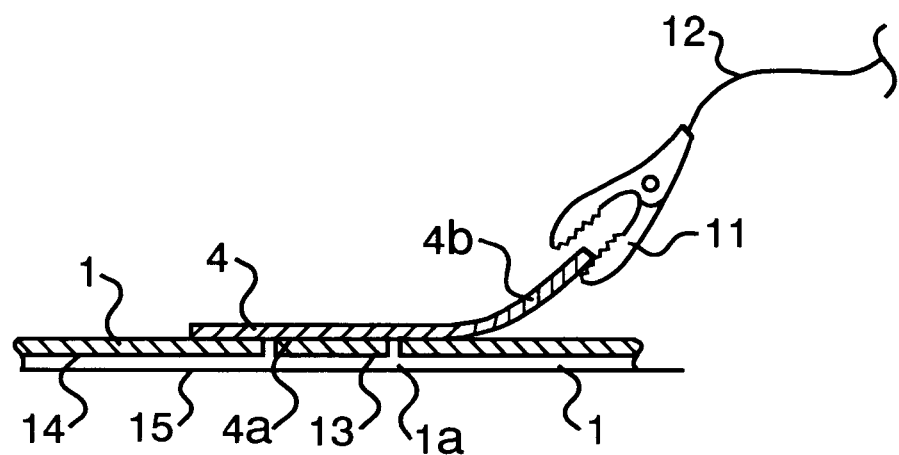
Figure 3:
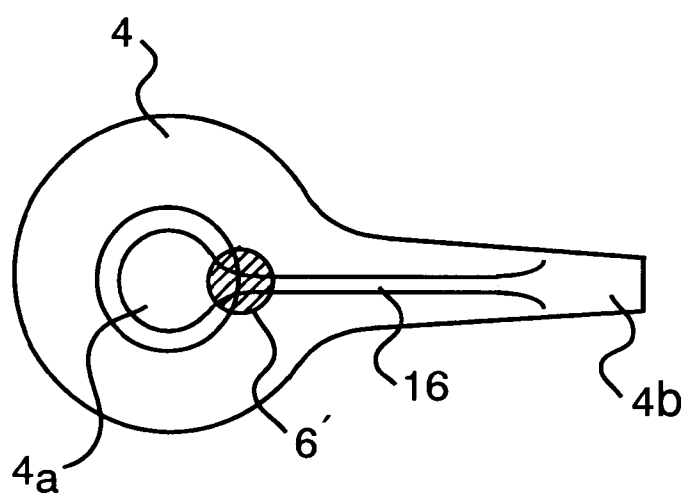
Figure 4:
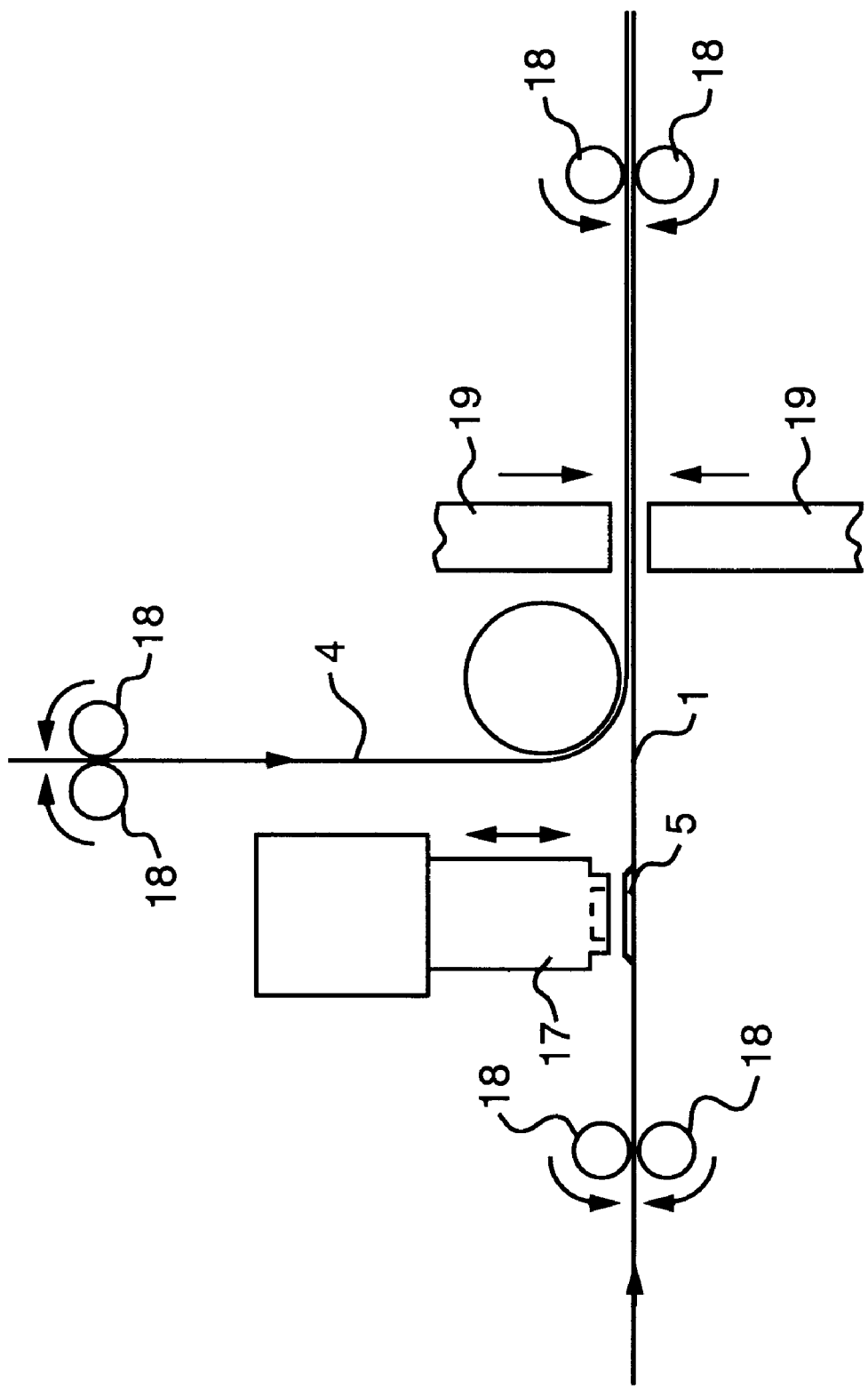

FIG. 1 diagrammatically shows an apparatus according to the invention for carrying out an embodiment of the process according to the invention, FIG. 2 is a view in section of an electrode produced by the process according to the invention or with an apparatus according to the invention, FIG. 3 shows the underside of a tag portion which can be used in connection with the process or the apparatus according to the invention, and FIG. 4 shows a further embodiment of an apparatus according to the invention for the production of an electrode which can be stuck on to the skin.

In the embodiment illustrated in FIG. 1 a web of carriers 1 is moved in the direction of the arrow 2. The individual electrodes are then later formed from that web in per se known manner along the separation lines 3 or by being stamped out. Initially however the web is a continuous web which can be easily moved by way of per se known transport apparatuses which are therefore not shown.

The aim of the process according to the invention is to stick a tag portion 4 on to each carrier 1, more specifically above an opening 1a in the carrier 1, which for example can be previously stamped out in a stamping procedure (not shown). Finally, at its underside, in the region of its opening 1a of the carrier 1 the tag portion 4 is to form an electrical sensor region 4a which is electrically connected to the laterally displaced contact region 4b for the connection of an electrode cable. At the same time the tag portion 4 is to be firmly and sealingly connected to the carrier 1.

For that purpose the embodiment of FIG. 1 has an electrically conductive tag portion 4 and, in accordance with the basic idea of the invention, the adhesive 5 is applied to the carrier 1 only in a locally delimited portion. In the illustrated embodiment the application of adhesive is in an annular configuration around the opening 1a, that is to say only on a part of the region of overlap between the tag portion 4 and the carrier 1. That annular application of adhesive provides for sealing integrity as between the tag portion 4 and the carrier 1, around the opening 1a.

In principle the locally delimited application of adhesive could also occur on the underside of the tag portions 4. In this respect however an essential consideration is that the electrically conductive underside of the tag portion is not covered over by adhesive in that region which later comes to lie in the region of the opening 1a of the carrier 1, because otherwise the electrical contact between the sensor region of the tag portion and the skin would be interrupted.

To provide for the locally delimited application of adhesive, the embodiment of FIG. 1 has a plurality of nozzles 7 which are controlled in respect of their period of opening and past which the carrier web is moved. In the illustrated embodiment the nozzles are arranged in two fixed, mutually displaced rows of nozzles which are arranged transversely to the direction of movement 2 of the carrier web. The programmable electronic control unit 8 controls the period of opening and the time of opening of the nozzles of the adhesive applicator device 10, by way of a control bus. When the speed of movement of the web of carriers 1 is known, by suitable matching of the opening time and the period of opening of the nozzles, it is possible by means of the nozzles to apply precise, locally delimited adhesive patterns to the carriers, for example in the present case an application of adhesive which extends around the opening 1a in an annular configuration. In that respect the individual spots of adhesive can be so closely adjacent that they merge together and overall afford a closed ring of adhesive (portion 6). The tag portion 4 which is supplied for example from the side is then stuck on to that portion 6 and pressed firmly thereon. Thereupon the individual carriers 1 can be cut or stamped out of the carrier web to form the individual electrodes.

The nozzles may also be disposed diagonally with respect to the direction of travel. With the same distances between the nozzles, a diagonal arrangement provides that the droplets of adhesive from adjacent nozzles are closer to each other.

In the process according to the invention the application of adhesive occurs in the production installation itself (and therefore 'in line'), more specifically as closely as possible prior to the making of the connection between the tag portions 4 and the carriers 1. In that way it is also possible to apply permanently active adhesives. In principle however it is also possible to apply adhesives which are not permanently active, that is to say activatable adhesives, such as for example melt adhesives.

FIG. 2 shows an embodiment of an electrode which is produced with the process according to the invention. In per se known manner, on its underside, the carrier 1 has a self-adhesive, skin-compatible layer 14 which is covered over by a cover film or sheet 15 for transportation and storage purposes. The cover film 15 also covers over an electrically conducting gel 13 provided in the region of the opening 1a of the carrier 1. A tag portion 4 is glued fast on to the carrier 1 on the top side by means of locally applied adhesive. The tag portion 4 comprises electrically conductive material. In relation to the central sensor region 4a which is in contact with the skin by way of the gel 13 the tag portion 4 has a laterally displaced, freely projecting projection (tongue 4b), to which an electrode cable 12 can be connected for example by way of a crocodile clip 11.

As already mentioned the tag portion 4 may be entirely of electrically conductive material, in which respect not only metals but also electrically conductive plastic materials or for example carbon fall to be considered. It is however also possible for the tag portion 4 to comprise an electrically insulating material and to be provided, for example coated, with conductive material on the whole of the underside which is towards the carrier 1. At any event the locally delimited application of adhesive prevents the sensor region 4a from being covered over by adhesive and thus losing its conductivity towards the skin.

FIG. 3 shows a further embodiment of a tag portion which is connected to a carrier by means of the process according to the invention. FIG. 3 is a view on to the underside of the tag portion, that is to say that side which then comes to lie on the top side of the carrier. An activatable, for example heat-activatable adhesive layer is initially provided entirely on that underside of the tag portion 4.

Printed on to that adhesive layer is an electrical conductor track 16 in layer form, which constitutes on the one hand a sensor region 4a and on the other hand a contact region 4b. After the tag portion has been put on to the carrier, it can be stuck to the carrier for example by the application of heat. In that operation however no glueing effect would occur in the region of the conductor track 16. In order here nonetheless to achieve a glueing effect it is possible for an adhesive additionally to be locally applied in the closely delimited portion 6', and that adhesive seals off the conductor track 16 towards the carrier.

FIG. 4 shows an embodiment of an apparatus according to the invention which, instead of nozzles, has a pad-type printing unit 17 in order to stamp adhesive 5 on to the web of the carriers 1 on locally delimited regions. Both the web of the carriers 1 and the web of the tag portions 4 are driven by way of transport devices 18 which are known per se. Tag portions 4 and carriers 1 are brought together in a joining station 19 downstream of the adhesive-applicator unit 17. The tag portions can then be stamped or cut out of the web. A screen printing unit is also noted.

What is claimed is:

1. An apparatus for producing adhesive electrodes for application to the skin, each electrode being provided with a carrier having a side near the skin and a side remote from the skin and an opening and with at least a partially electrically conductive tag glued to the carrier on the side remote from the skin, and wherein said tag covers said opening; the apparatus comprising;

a device for transporting carriers, a device for transporting tags, an adhesive application unit for applying an adhesive in a locally delimited region to the carriers or tags, a joining station downstream of the adhesive application unit for joining and gluing together the carriers and tags so that an electrically conductive area of each tag located in the region of the opening in each carrier remains free of adhesive.

2. The Apparatus of claim 1 wherein the adhesive applicator unit comprises a plurality of stationary nozzles which are controlled in respect to their period of opening and by way of which adhesive can be locally specifically applied to the moving carrier tag portions.

3. The Apparatus of claim 2 wherein the adhesive applicator unit comprises a printing unit for locally applying the adhesive.

* * * * *